United States Patent [19]
White et al.

[11] Patent Number: 5,405,511
[45] Date of Patent: Apr. 11, 1995

[54] BIOSENSING METER WITH AMBIENT TEMPERATURE ESTIMATION METHOD AND SYSTEM

[75] Inventors: Bradley E. White, Indianapolis; Michael L. Brown, Greenwood; Paul G. Ritchie, Indianapolis; Vladimir Svetnik, Carmel; Robert A. Parks, Springport; Stefan Weinert, Fortville, all of Ind.

[73] Assignee: Boehringer Mannheim Corporation, Indianapolis, Ind.

[21] Appl. No.: 73,179

[22] Filed: Jun. 8, 1993

[51] Int. Cl.⁶ ............................................. G01N 27/26
[52] U.S. Cl. ............................. 204/153.1; 204/153.12; 204/403; 204/408
[58] Field of Search ............... 204/408, 403, 406, 407, 204/153.1, 153.12

[56] References Cited
U.S. PATENT DOCUMENTS
4,420,564  12/1983  Tsuji et al. ........................... 435/288
5,108,564   4/1992  Szuminsky et al. ............. 204/153.12

FOREIGN PATENT DOCUMENTS
0471986A2  2/1992  European Pat. Off.

Primary Examiner—John Niebling
Assistant Examiner—Bruce F. Bell
Attorney, Agent, or Firm—Perman & Green

[57] ABSTRACT

A biosensing meter is provided that determines a value of an analyte in a biological sample. The meter employs an algorithm for determining the analyte value, which value is dependent upon ambient temperature about the biological sample when it is present in a reaction zone. The biosensing meter includes a processor and a temperature sensor. The temperature sensor is positioned within the meter's structure and thereby exhibits a delayed response to changes in the ambient temperature. The meter performs a temperature estimation method to overcome the delayed temperature response. The method commences by the meter repetitively and periodically acquiring temperature readings from the temperature sensor when the biosensing meter is both in an on state and in an off state. When the meter is in the on state, the algorithm estimates the ambient temperature by employing at least two most recent temperature readings and extrapolating therefrom to achieve an ambient temperature estimate. Temperature readings are acquired by the meter at first intervals when the meter is in the off state and at second, shorter intervals when the meter is in the on state, the temperature extrapolations only occurring when the meter is in the on state.

9 Claims, 3 Drawing Sheets

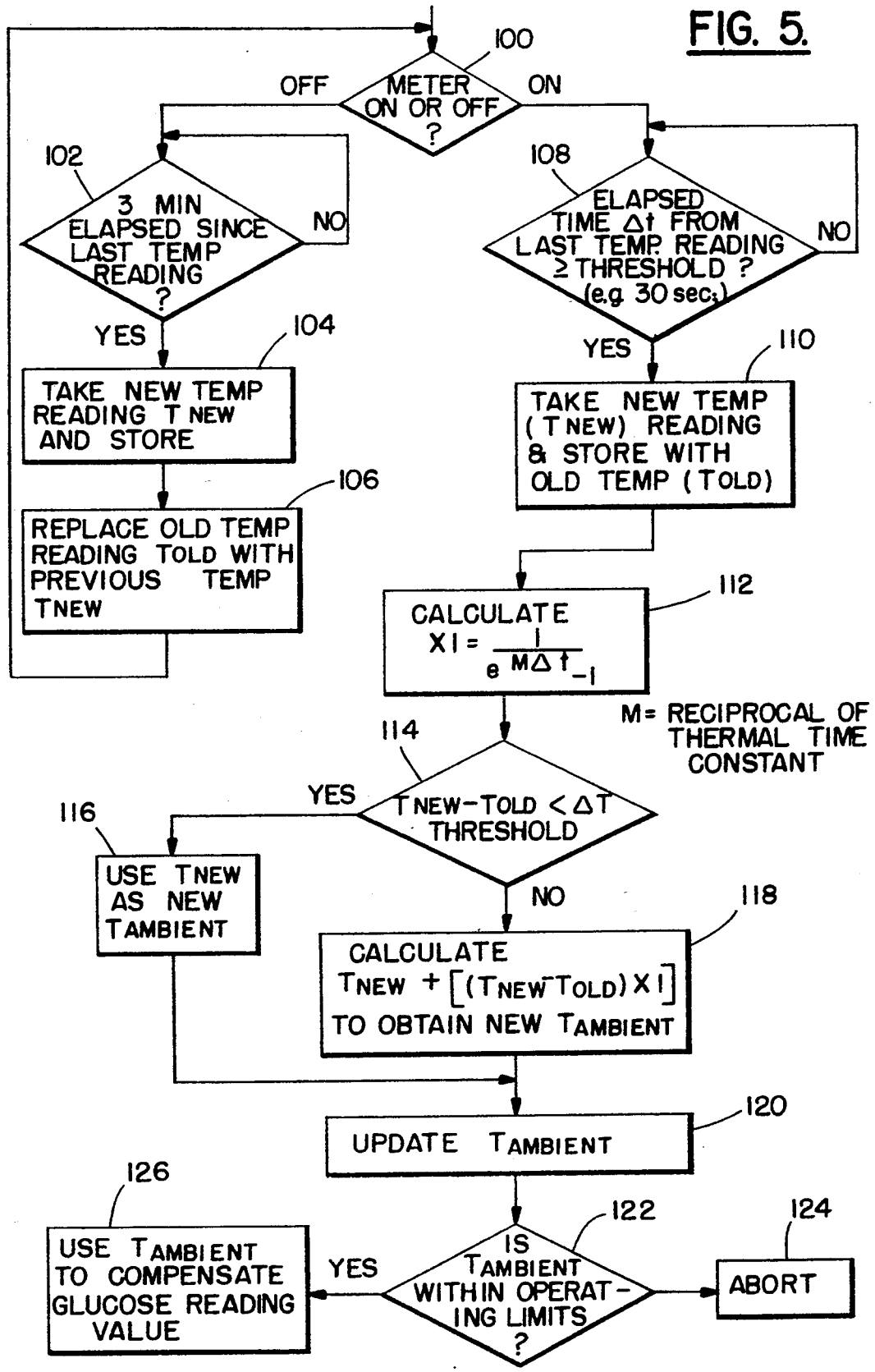

BIOSENSING METER WITH AMBIENT TEMPERATURE ESTIMATION METHOD AND SYSTEM

FIELD OF THE INVENTION

This invention relates to biosensing meters for determining the presence of an analyte in a biological sample, such determination sensitive to ambient temperature, and more particularly, to a method and system for estimating such ambient temperature.

BACKGROUND OF THE INVENTION

Biosensing instruments are often used for the detection of various analyte levels in blood samples (e.g., glucose and cholesterol). Such instruments employ disposable sample strips with a well or reaction zone for receiving a blood sample. Analyte readings obtained from such instruments are dependent upon the ambient temperature that surrounds the sample well or reaction zone. Various prior art instruments employ external thermal sensors or make an attempt to control the temperature of the reaction zone. While external temperature sensors are capable of rapidly reacting to a temperature change, under certain circumstances that becomes a detriment rather than an attribute. For instance, if a biosensing instrument is small enough to be held in a user's hand, when that instrument is placed on a table-top, a rapid temperature change can occur that will render invalid subsequent biochemical readings—until the ambient temperature reading has stabilized. If the biosensing instrument is battery-driven, it becomes impractical to control the temperature at the reaction zone as such action requires too great a power drain from the instruments battery.

The prior art includes a number of disclosures of biosensing instruments that employ temperature correction. In U.S. Pat. No. 5,108,564 to Szuminsky et al, a biosensing instrument is disclosed that measures glucose concentrations in blood. The instrument depends upon a reaction wherein glucose, in the presence of an enzyme, catalyzes a reaction of potassium ferricyanide to potassium ferricyanide. After the reaction has completed, a voltage is applied across a reaction zone and causes a reversal of the reaction, with an accompanying generation of a small, but measurable current. That current is termed the Cottrell current and, in dependence upon the concentration of glucose in the reaction zone, follows a predetermined curve during the reverse reaction. By determining the position of the curve, an indication of glucose concentration can be obtained.

European Patent application 047198682 of Tsutsumi et al discloses a blood glucose measurement system that employs disposable sample strips. The Tsutsumi et al system detects the presence of a blood sample by sensing a resistance across a pair of electrodes. It further employs plurality of sample-like strips, each having a specific resistance value which distinguishes it from other strips. Each of those strips has a particular application, i.e., for use during an adjustment mode of the instrument, during an error compensation mode; during a calibration mode; etc.

U.S. patent application Ser. No. 07/451,309, filed Dec. 15, 1989 to White and entitled "Biosensing Instrument and Method" and assigned to the same assignee as this application, teaches a biosensing instrument which employs the "Cottrell" curve relationship to determine glucose concentrations. In the White patent application, a ratio between current samples and times at which the current samples are taken is used to determine whether the current flow through a sample strip's reaction zone is, in fact, following the Cottrell relationship.

U.S. Pat. No. 4,420,564 to Tsuji et al. describes a blood sugar analyzer that employs a reaction cell having a fixed enzyme membrane sensor and a measuring electrode. The Tsuji et al. system includes several fail/safe procedures, one to determine that the reaction is taking place within specifically defined temperature limits and a second to determine if a reaction current remains within a predetermined range.

In the above noted prior art that indicates a need for temperature sensing, temperature values are obtained by temperature sensors and those sensed values are directly used. Variations in those sensed temperatures can create substantial variation in biochemical readings and cause erroneous outputs. Since such readings are of vital importance to the user and, if erroneous, may result in the mis-administration of medications, it is vital that erroneous readings be avoided. Thus, such biosensing instruments must include means for avoiding erroneous readings that result from erroneous ambient temperature inputs.

Accordingly, it is an object of this invention to provide a biosensing instrument with a method and means for providing accurate temperature values so as to enable proper analyte value indications.

It is another object of this invention to provide a biosensing instrument with a temperature sensor that is resistant to rapid temperature excursions as result of environmental changes, but still provides accurate ambient temperature values to enable analyte determinations.

SUMMARY OF THE INVENTION

A biosensing meter is provided that determines a value of an analyte in a biological sample. The meter employs an algorithm for determining the analyte value, which value is dependent upon ambient temperature about the biological sample when it is present in a reaction zone. The biosensing meter includes a processor and a temperature sensor. The temperature sensor is positioned within the meter's structure and thereby exhibits a delayed response to changes in the ambient temperature. The meter performs an ambient temperature estimation method to overcome the delayed temperature response. The method commences by the meter repetitively and periodically acquiring temperature readings from the temperature sensor when the biosensing meter is both in an on state and in an off state. When the meter is in the on state, the algorithm estimates the ambient temperature by employing at least two most recent temperature readings and extrapolating therefrom to achieve an ambient temperature estimate. Temperature readings are acquired by the meter at first intervals when the meter is in the off state and at second, shorter intervals when the meter is in the on state, the temperature extrapolations only occurring when the meter is in the on state.

DESCRIPTION OF THE DRAWINGS

FIG. 5 is a high level flow diagram illustrating the procedure followed by the method of the invention.

DETAILED DESCRIPTION OF THE INVENTION

Figure 1:
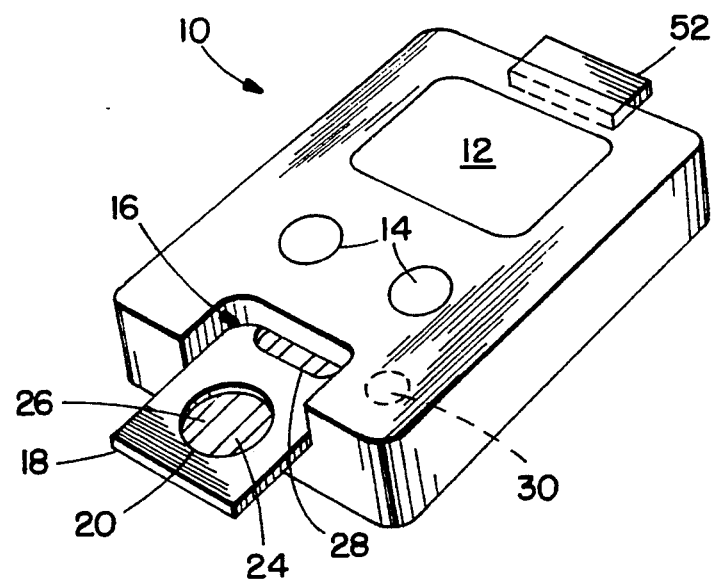
FIG. 1 is a perspective view of a biosensing meter incorporating the invention.

Referring now to FIG. 1, a biosensing meter 10 includes a liquid crystal display 12, control buttons 14, and a slot 16 for receiving a disposable sample strip 18. Sample strip 18 contains a well 20 (i.e. reaction zone) that encompasses a pair of conductive electrodes 24 and 26. A layer (not shown) of enzymatic reactants overlays electrodes 24 and 26 in well 20 and provides substrate on which an analyte-containing fluid sample may be emplaced.

Disposable sample strip 18 has an opening 28 that exposes the distal ends of electrodes 24 and 26 and renders them available for electrical connection within biosensing meter 10 (electrical connections not shown in FIG. 1).

A temperature sensor 30 (shown in phantom) is positioned within the case of biosensing meter 10 and provides continuing temperature value inputs to a microprocessor contained within biosensing meter 10. The position of temperature sensor 30 within biosensing meter 10 causes it to be insulated from immediate temperature changes that occur in the ambient about the meter's exterior. As a result, temperature sensor 30 will respond to a change in ambient temperature, but will do so in a delayed manner and over a plurality of thermal time constants, the length of the time constant being a function of the isolation of temperature sensor 30 from the ambient.

Figure 2:
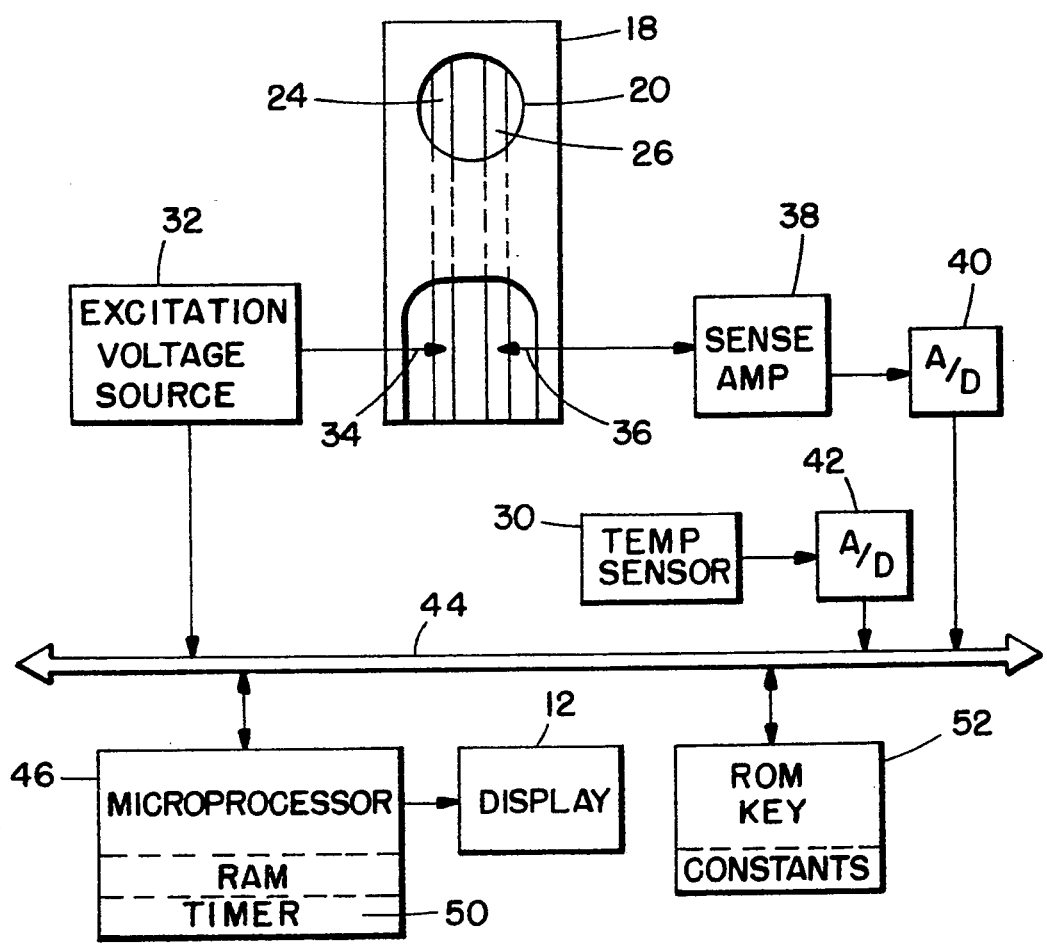
FIG. 2 is a block diagram of circuitry contained within the biosensing meter of FIG. 1.

Referring to FIG. 2, a schematic is shown of circuitry within biosensing meter 10, with a disposable sample strip 18, inserted in slot 16. An excitation voltage source 32 provides a variable voltage to a contact 34 that makes connection with electrode 24 when disposable sample strip 18 is in position within meter 10. A contact 36 enables a current from electrode 26 to be fed to a sense amplifier 38 whose output (a voltage) is, in turn, fed to an analog to digital converter (A/D) 40. Temperature sensor 30 also provides its output to an A/D converter 42. The outputs from A/D converters 40 and 42 are applied to a bus 44 which provides communications between modules contained within biosensing meter 10. A microprocessor 46, with an allied display unit 12, provides overall control of the operation of biosensing meter 10. Microprocessor 46 also has a variety of timing functions 50 contained therein whose use will become apparent from the description below.

Excitation voltage source 32 receives its commands from microprocessor 46 via bus 44, and response to those commands applies varying levels of excitation potential to electrode 24. A read only memory key 52 is pluggable into biosensing meter 10 and contains a nonvolatile memory that includes constants and other data required to carry out the analyte-determination procedures required of meter 10. ROM key 52 plugs into the upper most portion of meter 10 as shown in FIG. 1. In general, a ROM key 52 will accompany each batch of disposable sample strips 18, and will contain various constants that will enable meter 10 to adjust its measurement parameters to match the specific batch characteristics of disposable sample strips 18.

In this example, it will be assumed that the analyte-containing sample is a drop of blood that is being subjected to a glucose determination. A disposable sample strip for a glucose determination will include, in well 20, the following reactants: an enzyme, an electrolyte, a mediator, film formers, and a buffer. For instance, the enzyme may be glucose oxidase or glucose dehydrogenase; the buffer may be organic or inorganic; the electrolyte may be potassium chloride or sodium chloride; the mediator is preferably potassium ferricyanide and the film formers comprise gelatin and propiofin. (If the test cell is to be employed for a cholesterol concentration determination, the enzyme would preferably be cholesterol oxidases, with or without a cholesterol esterase additive. The buffer would be preferably inorganic and would include an electrolyte such as potassium chloride or sodium chloride. In this case two mediators would be used, i.e. ferricyanide and quinones, and would be placed in the gelatin film as indicated above.)

As the chemistry employed to make such analyte determinations are known in the art, they will not be described in significant detail. Suffice to say that a glucose determination is made by initially emplacing in well 20, a sample of blood. The glucose within the sample causes a forward reaction of potassium ferricyanide to potassium ferricyanide. The forward reaction proceeds to completion during an incubation period. A subsequent application of an excitation voltage to an electrode in disposable sample strip 18 will see the creation of a small current at the opposite electrode that results from a reverse reaction of potassium ferricyanide back to potassium ferricyanide. The flow of electrons during the reverse reaction is sensed and measured at a number of points so as to enable determination that the reaction is both following a Cottrell curve and to further determine the level of the Cottrell curve. That level is indicative of the glucose concentration. Any resultant glucose value, however, must be corrected to take into account the ambient temperature.

Figure 3:
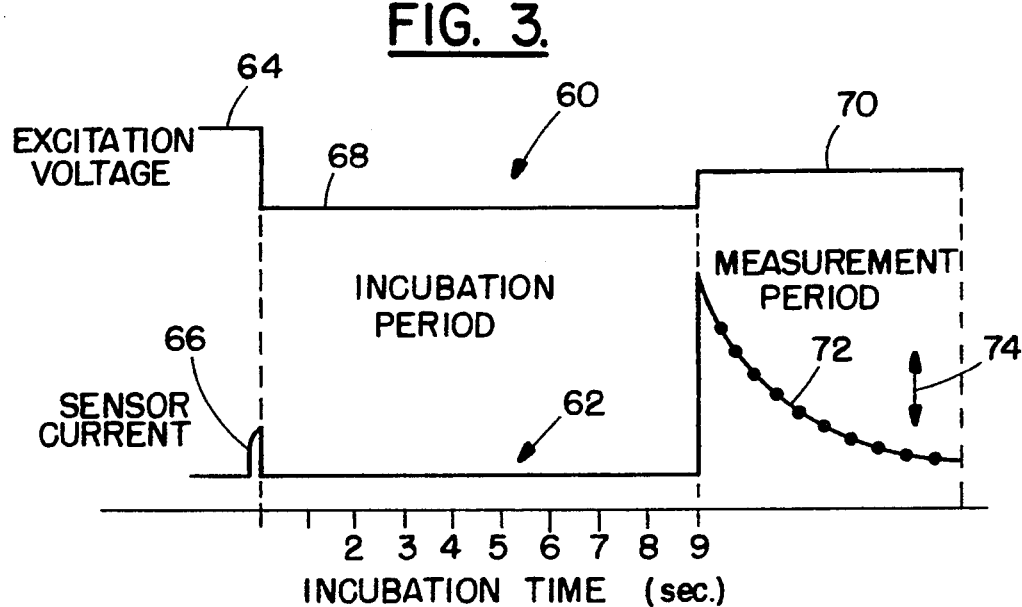
FIG. 3 is a waveform diagram illustrating both an excitation voltage applied to an excitation electrode of a disposable sample strip used with the meter of FIG. 1 and a resulting sense current determined from a sense electrode on the disposable sample strip.

The excitation potentials supplied by excitation voltage source 32 to electrode 24 are shown by trace 60 in FIG. 3. The resulting sense current, as determined by sense amplifier 38, is shown by trace 62. Initially, excitation voltage source 32 applies a level 64 to electrode 24. When a blood sample is placed in well 20, a current pulse 66 results, indicating to microprocessor 46 to commence an incubation period. At such time, the excitation voltage level 64 is removed from electrode 24 (level 68) to enable a reaction to occur between the drop of blood and the reactants. At the end of the incubation period, excitation voltage source 32 applies a voltage level 70 to electrode 24. In response, sense amplifier 38 detects and measures a number of currents flowing to electrode 26 (as shown by trace 72).

Assuming that the current sensed across well 20 is following the Cottrell relationship, the current values sensed along curve 72 will be displaced either upwardly or downwardly dependent upon the level of glucose present in the blood sample. Microprocessor 46, in conjunction with ROM key 52 employs the measurements taken along curve 72 to determine the position of curve 72 and derives a glucose value therefrom. In order to alter the resultant glucose value so determined, the ambient temperature must be determined and a correction applied. Only after such correction is made, is the glucose value displayed to the user on display 12.

Figure 4:
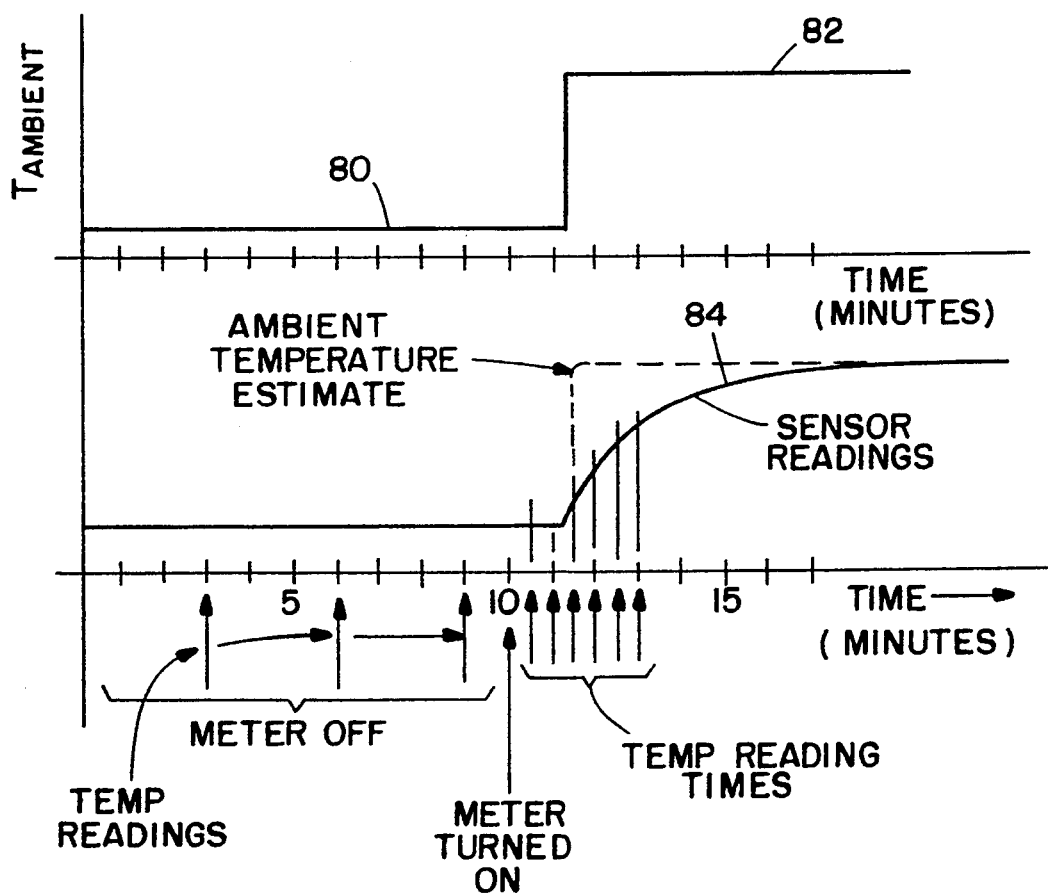
FIG. 4 indicates a change in ambient temperature and a resulting change in temperature as sensed at a temperature sensor within the meter FIG. 1.

Turning to FIGS. 4 and 5, the temperature estimation procedure employed by a biosensing meter 10 will be described. Because it is desired to isolate temperature sensor 30 from rapid thermal changes, temperature sensor 30 is mounted within biosending meter 10 so as to be somewhat isolated from the ambient temperature. As a result, when an ambient temperature change occurs, thermal sensor 30 will begin to alter its output in accordance therewith, but will only arrive at the actual ambient temperature after plural thermal time constants have passed. One thermal time constant for biosensing meter 10 is the time required for temperature sensor 30 to traverse approximately 60 percent of the temperature difference between the beginning temperature of thermal sensor 30 and the actual ambient temperature.

In one meter that has been constructed in accordance with this invention, the thermal time constant is approximately ten minutes. In order for temperature sensor 30 to traverse ninety-eight percent of the temperature between the beginning temperature of thermal sensor 30 and ambient, the passage of four time constants or forty minutes is required-if biosensing meter 10 is to wait for such an occurrence.

Clearly, it is not desirable for the user to wait for forty minutes to obtain an accurate glucose reading. As a result, it has been determined that accurate glucose readings can be obtained by estimating the ambient temperature from a few temperature readings from temperature sensor 30. Those readings are obtained over a short period of time, e.g., characteristically less than one minute. In order to achieve such an estimation of temperature, at least two temperature sensings must be available for calculation by microprocessor 46. One such temperature reading will hereafter be referred to as $T_{old}$ and a later temperature reading will be referred to as $T_{new}$.

So as to not require a user to wait for two temperature readings to be obtained, biosensing meter 10 is caused to take temperature readings at periodic intervals even when it is in the off state. In such off state, sufficient power is provided to microprocessor 46 that microprocessor 46 takes a temperature reading from temperature sensor 30 every three minutes. That temperature reading is stored as $T_{new}$ while the former $T_{new}$ replaces the previous $T_{old}$ value stored in RAM within microprocessor 46. Clearly, those skilled in the art will realize that the time of three minutes is not critical and may be varied in accordance with the meter's requirements.

When meter 10 is subsequently powered on by the user, microprocessor 46 then obtains readings from temperature sensor 30 every thirty seconds to obtain $T_{new}$ values. The first such $T_{new}$ reading after a power on is combined with the $T_{old}$ reading already stored in RAM in microprocessor 46. From those two readings, an initial extrapolation is made to determine $T_{ambient}$. Thereafter, new temperature readings $T_{new}$ are taken and at each such time, a $T_{old}$ value is dropped and is replaced by the previous $T_{new}$ reading which becomes the $T_{old}$ value. In such a manner, meter 10 is able to provide $T_{ambient}$ values very rapidly after power on and proper glucose value modifications can be made in accordance therewith.

Referring to FIG. 4, it is assumed that $T_{ambient}$ varies from level 80 to level 82. Also, it is assumed that meter 10 is in an off state until 10 minutes have passed at which time it is turned on. Until time t=10, temperature readings are taken every three minutes (during the off state) and are stored. When the meter is turned on, temperature readings begin being taken every thirty seconds and temperature extrapolations made after every such reading. When $T_{ambient}$ changes from level 80 to level 82, the output 84 from temperature sensor 30 begins to approach the new ambient temperature (level 82) in an exponential fashion. Output temperature reading values from temperature sensor 30, taken during this time, enable microprocessor 46 to render an estimation of $T_{ambient}$ in accordance with the following relationship:

$$T_{ambient} = T_{new} + \frac{T_{new} - T_{old}}{e^{m\Delta t} - 1} \tag{A}$$

Where:
  m=inverse of the meter's thermal time constant (in seconds); and
  $\Delta t$=the time in seconds between acquisition of $T_{new}$ and $T_{old}$.

Referring to FIG. 5, the ambient temperature estimation procedure employed by microprocessor 46 will be described. As indicated by decision box 100, if meter 10 is off, a determination is made whether three minutes have elapsed since the last temperature reading (decision box 102). If three minutes have not elapsed, the procedure recycles. Upon the passage of three minutes, a new temperature reading $T_{new}$ is taken (box 104). The old temperature reading $T_{old}$ is replaced with the previous temperature reading $T_{new}$ (box 106). The procedure then recycles to again determine whether meter 10 has been turned on or off.

Once meter 10 is turned on, the elapsed time $\Delta t$ from the last temperature reading is determined and compared to a threshold time value obtained from memory. If the $\Delta t$ value exceeds the threshold value (e.g. thirty seconds), a new temperature reading $T_{new}$ is taken and stored with $T_{old}$ (box 110). If the elapsed time $\Delta t$ is less than the threshold time value, the procedure recycles to wait for the expiration of a proper amount of time.

The aforesaid threshold time value for $\Delta t$ is employed to prevent microprocessor 46 from making extrapolations based upon temperature readings that are taken too close together in time. Such readings could cause a substantial error which would skew the temperature estimate. As can be seen from equation A, as the value of $\Delta t$ decreases, the value of $e^{\Delta t}$ approaches unity. As a result, if $\Delta t$ is too small the $1/(e^{m\Delta t}-1)$ factor becomes large. This factor can greatly multiply small errors in the measurement of $T_{new}$ and $T_{old}$ and result in an erroneous skew in the ultimate $T_{ambient}$ calculated value. Once a new temperature reading $T_{new}$ is taken, a portion of equation A is calculated (box 112) as follows:

$$X1 = \frac{1}{e^{m\Delta t} - 1} \tag{B}$$

Once equation B is calculated, it is determined whether the new sensed temperature $T_{new}$ minus the old temperature $T_{old}$ is less than a temperature threshold value $\Delta T$ (decision box 114). Threshold value $\Delta T$ is obtained from ROM key 52. In the case where both $T_{new}$ and $T_{old}$ are very close, it is possible that the estimation algorithm can actually show a significant movement in temperature when, in fact, the difference could entirely be due to noise. Therefore, the difference between $T_{new}$ and $T_{old}$ is compared to a temperature estimation threshold $\Delta T$ obtained from ROM key 52. If the temperature difference is greater than the $\Delta T$ threshold value, then a full temperature estimation is warranted. If, however, the difference between the temperature samples is less than the $\Delta T$ value obtained from ROM key 52, the temperature samples are assumed to be essentially identical and no temperature movement is assumed to have been seen during the entire $\Delta t$ (indicating that meter 10 is probably at equilibrium). Therefore, no estimation is needed and $T_{new}$ may be used as the new ambient temperature If, by contrast, the temperature difference between $T_{new}$ and $T_{old}$ is equal to or exceeds the $\Delta T$ threshold value, equation (C) is calculated as shown in box 118:

$$T_{ambient} = T_{new} + [(T_{new} - T_{old})X1] \qquad (C)$$

Equation (C) allows a new $T_{ambient}$ estimate to be obtained. The previously stored value of $T_{ambient}$ is then updated with the new value (box 120). The new value $T_{ambient}$ is then compared with operating limit values obtained from ROM key 52 (decision box 122). If $T_{ambient}$ is not within proper operating limits, the test is aborted (box 124). If $T_{ambient}$ is found to be within proper operating limits, then $T_{ambient}$ is employed to compensate the glucose reading value (box 126). Such operating limit values are the limits of the temperature correction algorithm, (e.g., between 18° C. and 32° C.).

It should be understood that the foregoing description is only illustrative of the invention. Various alternatives and modifications can be devised by those skilled in the art without departing from the invention. For example, while two A/D converters 40 and 42 are shown in FIG. 2, a single A/D converter for both inputs will operate equally well. Accordingly, the present invention is intended to embrace all such alternatives, modifications and variances which fall within the scope of the appended claims.

We claim:

1. A temperature estimation method for use in a biosensing meter that determines a value of an analyte in a biological sample, a determined analyte value dependent upon an ambient temperature about said biological sample, said biosensing meter including a processor and a temperature sensor, said temperature sensor positioned within said meter and thereby exhibiting a delayed response to changes in said ambient temperature, said temperature estimation method controlled by said processor to overcome said delayed response, and comprising the steps of:
    (a) periodically acquiring temperature readings from said temperature sensor when said biosensing meter is both in an ON state and in an OFF state;
    (b) when said biosensing meter is in said ON state, estimating said ambient temperature by employing at least two most recent temperature readings; and
    (c) employing said ambient temperature estimated in step (b) to compensate a determined analyte value.

2. The method as recited in claim 1 wherein step b estimates said ambient temperature by using said two most recent temperature readings and extrapolating therefrom to determine said estimate of said ambient temperature.

3. The method as recited in claim 2 wherein said temperature readings are acquired at first intervals when said meter is in said OFF state, and at second, shorter intervals when said meter is in said ON state, said biosensing meter employing a temperature reading acquired when said meter is in said OFF state and a temperature reading when said meter is in said ON state to determine at least one said temperature estimate.

4. The method as recited in claim 1 wherein said estimation step is only performed when a difference between said two most recent temperature readings exceeds a threshold value, a latest temperature reading being employed as said ambient temperature when said threshold value is not exceeded.

5. The method as recited in claim 1 wherein said estimation step extrapolates said two most recent temperature readings $T_{old}$ and $T_{new}$ to obtain $T_{ambient}$ by employing the expression:

$$T_{ambient} = T_{new} + \frac{(T_{new} - T_{old})}{e^{m\Delta t} - 1}$$

Where:
    m = inverse of the meter's thermal time constant (in seconds);
    $\Delta t$ = the time in seconds between acquisition of $T_{new}$ and $T_{old}$.

6. The method as recited in claim 5 wherein $T_{old}$ is acquired when said meter is in said OFF state, and said meter is switched to the ON state and a $T_{new}$ reading is acquired, the method comprising the added steps of:
    determining an elapsed time between when $T_{old}$ and $T_{new}$ values are acquired;
    comparing said determined elapsed time against a time threshold; and
    disregarding said $T_{new}$ reading when said elapsed time is not at least equal to said elapsed time threshold.

7. The method as recited in claim 5, comprising the following added steps of:
    finding a temperature difference value between $T_{new}$ and $T_{old}$;
    comparing said temperature difference value with a temperature difference threshold value; and
    employing $T_{new}$ reading as a new $T_{ambient}$ value when said temperature difference value is less than said temperature difference threshold value, based upon an assumption that said biosensing meter is at a stable temperature.

8. The method as recited in claim 7 wherein said biosensing meter includes a pluggable read only memory chip, and wherein said temperature difference threshold value is acquired from said pluggable read only memory chip.

9. The method as recited in claim 5, wherein said biosensing meter operates when said $T_{ambient}$ falls within set operating temperature limits.

* * * * *